United States Patent [19]

Bencze et al.

[11] Patent Number: 4,945,092
[45] Date of Patent: Jul. 31, 1990

[54] SUBSTITUTED 1-(OXOPYRROLIDINYLALKANOYL)-PIPERAZINES USEFUL AS NOOTROPICS

[75] Inventors: William Bencze, Therwil; Wolfgang Fröstl, Basel; Max Wilhelm, Riehen, all of Switzerland

[73] Assignee: Ciba-Geigy Corporation, Ardsley, N.Y.

[21] Appl. No.: 370,093

[22] Filed: Jun. 19, 1989

Related U.S. Application Data

[60] Continuation of Ser. No. 191,671, May 9, 1988, abandoned, which is a division of Ser. No. 5,974, Jan. 21, 1987, abandoned.

[30] Foreign Application Priority Data

Jan. 30, 1986 [CH] Switzerland .................. 346/86

[51] Int. Cl.$^5$ .................. A61K 31/495; C07D 403/12; C07D 403/14
[52] U.S. Cl. ...................... 514/252; 544/372
[58] Field of Search ................... 544/372, 252

[56] References Cited

U.S. PATENT DOCUMENTS 3,459,738  8/1969  Morren ........................ 540/531
4,144,246  3/1979  L'Italien ...................... 548/551

OTHER PUBLICATIONS

CA 95:24693r (1981).

Primary Examiner—Cecilia Shen
Attorney, Agent, or Firm—JoAnn Villamizar

[57] ABSTRACT

Substituted pyrrolidin-2-ones of the formula

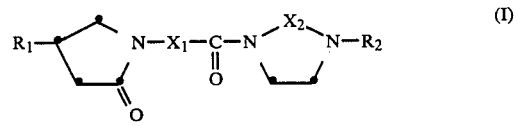
(I)

wherein $R_1$ represents a phenyl or naphthyl radical that is unsubstituted or substituted by lower alkyl, lower alkloxy, halogen and/or trifluoromethyl, $X_1$ represents lower alkylidene, $X_2$ represents methylene, ethylene or oxoethylene and $R_2$ represents hydrogen, lower alkyl or a radical of the formula

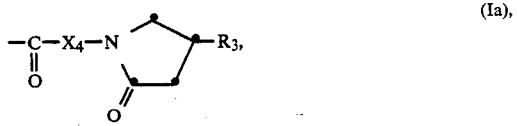
(Ia), wherein $X_4$ represents lower alkylidene and $R_3$ represents hydrogen or a phenyl or naphthyl radical that is unsubstituted or substituted by lower alkyl, lower alkoxy, halogen and/or trifluoromethyl, and their pharmaceutically acceptable salts, have nootropic properties and can be used as nootropic active ingredients in medicaments. They are prepared, for example, by condensing with one another compounds of the formulae

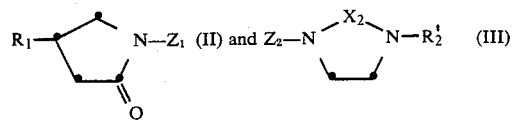

wherein $Z_1$ represents a group of the formula $-X_1-C(=O)-Z_3$ (IIa) and $Z_2$ reresents hydrogen, or $Z_1$ represents hydrogen and $Z_2$ represents a group of the formula $-C(=O)-X_1-Z_4$ (IIIa), wherein each of $Z_3$ and $Z_4$ represents a removable radical and $R'_2$ represents a radical $R_2$ or an amino-protecting group, or their salts, and removing an amino-protecting group $R'_2$ which may be present.

17 Claims, No Drawings

SUBSTITUTED 1-(OXOPYRROLIDINYLALKANOYL)-PIPERAZINES USEFUL AS NOOTROPICS

This application is a continuation of application Ser. No. 191,671, filed May 9, 1988, now abandoned, which is a divisional of application Ser. No. 5,974 filed Jan. 21, 1987, now abandoned.

The invention relates to substituted pyrrolidin-2-ones of the formula

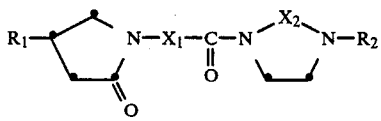 (I)

wherein $R_1$ represents a phenyl or naphthyl radical that is unsubstituted or substituted by lower alkyl, lower alkoxy, halogen and/or trifluoromethyl, $X_1$ represents lower alkylidene, $X_2$ represents methylene, ethylene or oxoethylene and $R_2$ represents hydrogen, lower alkyl or a radical of the formula

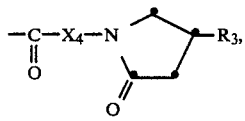 (Ia)

wherein $X_4$ represents lower alkylidene and $R_3$ represents hydrogen or a phenyl or naphthyl radical that is unsubstituted or substituted by lower alkyl, lower alkoxy, halogen and/or trifluoromethyl, in free form or in the form of salts, especially in the form of pharmaceutically acceptable salts, to processes for the manufacture of the compounds according to the invention, to pharmaceutical preparations containing them, and to their use as active ingredients in medicaments.

The radicals $X_1$ and $X_4$ may be identical or different. Likewise, an optionally substituted phenyl or naphthyl radical $R_3$ may be identical to $R_1$ or different from $R_1$.

The phenyl or naphthyl radical $R_1$ and, where appropriate, $R_3$ may be unsubstituted or may, as indicated, be monosubstituted or di- or poly-substituted, for example disubstituted or trisubstituted, by identical or different substituents selected from those indicated, and is, for example, phenyl that is optionally substituted, especially monosubstituted or disubstituted, as indicated, or unsubstituted naphthyl, for example 1-naphthyl or, in the second place, 2-naphthyl.

The radical $X_2$ is especially ethylene but, as mentioned, may also be oxoethylene or methylene.

Hereinbefore and hereinafter, there are to be understood by lower radicals and compounds, for example, those radicals and compounds which contain up to and including 7, preferably up to and including 4, carbon atoms (C atoms).

Lower alkyl is, for example, $C_1$–$C_7$-alkyl, preferably $C_1$–$C_4$-alkyl, such as methyl, ethyl, propyl, isopropyl or butyl, but may also be isobutyl, secondary butyl, tertiary butyl or a pentyl, hexyl or heptyl group.

Lower alkoxy is, for example, $C_1$–$C_7$-alkoxy, preferably $C_1$–$C_4$-alkoxy, such as methoxy, ethoxy, propoxy, isopropoxy or butoxy, but may also be isobutoxy, secondary butoxy, tertiary butoxy or a pentyloxy, hexyloxy or heptyloxy group.

Halogen is, for example, halogen having an atomic number of up to and including 35, such as chlorine or fluorine, or also bromine.

Lower alkylidene is, for example, terminally bonded lower alkylidene, such as corresponding $C_1$–$C_7$-alkylidene, preferably $C_1$–$C_5$-alkylidene, for example methylene, ethylidene, 1,1-propylidene or 1,1-(3-methyl)-butylidene (isopentylidene), but may also be 1,1-butylidene, 2,2-propylidene (isopropylidene) or 1,1-(2-methyl)-propylidene (isobutylidene).

Acid addition salts of compounds of the formula I are, for example, pharmaceutically acceptable salts with suitable mineral acids, such as hydrohalic acids, sulphuric acid or phosphoric acid, for example hydrochlorides, hydrobromides, sulphates, bisulphates or phosphates, or salts with suitable organic carboxylic or sulphonic acids, such as optionally hydroxylated aliphatic mono- or di-carboxylic acids, for example acetates, oxalates, succinates, fumarates, maleates, malates, ascorbates or citrates, or aliphatic or aromatic sulphonic acids or N-substituted sulphamic acids, for example methanesulphonates, benzenesulphonates, p-toluenesulphonates or N-cyclohexyl sulphamates (cyclamates).

For the purposes of isolation or purification, it is also possible to use pharmaceutically unsuitable salts. Only the pharmaceutically acceptable, non-toxic salts are used therapeutically, and these are therefore preferred.

The compounds of the formula I and their pharmaceutically acceptable salts have valuable pharmacological, especially nootropic, properties. For example, in mice, in doses of approximately 0.1 mg/kg and above i.p. and p.o., they reduce the amnesiogenic effect of an electric shock to at least the same extent as when a nootropically active dose of piracetam (100 mg/kg i.p.) has been administered. The Two-Compartment Test, for example, may be used to demonstrate the nootropic action.

There may be mentioned as literature relating to pharmacological models of this kind, for example: S. J. Sara and D. Lefevre, Psychopharmacologia 25, 32–40 (1972), Hypoxia-induced amnesia in one-trial learning and pharmacological protection by piracetam, Boggan, W. O. and Schlesinger, K., in Behavioral Biology 12, 127–134 (1974).

Furthermore, the compounds of the formula I exhibit a strong memory-improving effect in the Step-Down Passive Avoidance Test according to Mondadori and Waser, Psychopharmacology 63, 297–300 (1979). The substances are effective in the case of intraperitoneal administration 30 minutes before the learning test (effective doses 0.1, 1, 10 mg/kg). A marked effect could also be detected in the case of peroral administration 60 minutes before the learning test (effective doses 0.1, 1, 10 mg/kg) and in the case of intraperitoneal administration directly after the learning test (effective doses 0.1, 1, 10 mg/kg).

The compounds of the formula I and their pharmaceutically acceptable salts can accordingly be used as nootropics, for example for the treatment of cerebral insufficiency, especially memory disorders having various causes, such as senile dementia or dementia of the Alzheimer type, and also the sequelae of cerebral trauma and apoplexy.

The invention relates especially to compounds of the formula I wherein $R_1$ represents a phenyl or naphthyl radical that is unsubstituted or mono- or di-substituted by $C_1$–$C_4$-alkyl, $C_1$–$C_4$-alkoxy, halogen having an atomic number of up to and including 35 and/or by trifluoromethyl, $X_1$ represents $C_1$–$C_7$-alkylidene, $X_2$ represents methylene, ethylene or oxoethylene and $R_2$ represents hydrogen, $C_1$–$C_7$-alkyl or a group of the formula Ia wherein $X_4$ represents $C_1$–$C_7$-alkylidene and $R_3$ represents hydrogen or a phenyl or naphthyl radical that is unsubstituted or mono- or di-substituted by $C_1$–$C_4$-alkyl, $C_1$–$C_4$-alkoxy, halogen having an atomic number of up to and including 35 and/or by trifluoromethyl, and to their salts, especially pharmaceutically acceptable salts.

The invention relates above all to compounds of the formula I wherein $R_1$ represents phenyl that is unsubstituted or substituted by halogen having an atomic number of up to and including 35, such as chlorine, $C_1$–$C_4$-alkoxy, such as methoxy, $C_1$–$C_4$-alkyl, such as methyl, or by trifluoromethyl, or represents unsubstituted naphthyl, $X_1$ represents terminally bonded $C_1$–$C_7$-alkylidene, such as methylene, isobutylidene or isopentylidene, $X_2$ represents oxoethylene and $R_2$ represents hydrogen, and to their salts, especially pharmaceutically acceptable salts.

The invention relates especially to compounds of the formula I wherein $R_1$ represents phenyl that is unsubstituted or substituted by halogen having an atomic number of up to and including 35, such as chlorine, $C_1$–$C_4$-alkoxy, such as methoxy, $C_1$–$C_4$-alkyl, such as methyl, or by trifluoromethyl, or represents unsubstituted naphthyl, $X_1$ represents terminally bonded $C_1$–$C_4$-alkylidene, such as methylene or isobutylidene, $X_2$ represents oxoethylene bonded via the carbonyl group to the partial structure —N($R_2$)— and $R_2$ represents hydrogen, and to their salts, especially pharmaceutically acceptable salts.

The invention also relates especially to compounds of the formula I wherein $R_1$ represents phenyl that is unsubstituted or substituted by halogen having an atomic number of up to and including 35, such as chlorine, $C_1$–$C_4$-alkoxy, such as methoxy, $C_1$–$C_4$-alkyl, such as methyl, or by trifluoromethyl, or represents unsubstituted naphthyl, $X_1$ represents terminally bonded $C_1$–$C_7$-alkylidene, such as methylene or isopentylidene, or preferably terminally bonded $C_1$–$C_4$-alkylidene, such as methylene, $X_2$ represents methylene or ethylene and $R_2$ represents $C_1$–$C_4$-alkyl, such as methyl, or a group of the formula Ia wherein $X_4$ is terminally bonded $C_1$–$C_4$-alkylidene, such as methylene, and $R_3$ represents hydrogen, and to their salts, especially pharmaceutically acceptable salts.

The invention relates more especially to compounds of the formula I wherein $R_1$ represents phenyl that is unsubstituted or substituted by halogen having an atomic number of up to and including 35, such as chlorine, or represents unsubstituted naphthyl, $X_1$ represents terminally bonded $C_1$–$C_4$-alkylidene, such as methylene, $X_2$ represents oxoethylene bonded via the carbonyl group to the partial structure —N($R_2$)— and $R_2$ represents hydrogen, and to their salts, especially pharmaceutically acceptable salts.

The invention relates first and foremost to compounds of the formula I wherein $R_1$ represents phenyl that is unsubstituted or substituted by halogen having an atomic number of up to and including 35, such as chlorine, or represents unsubstituted napthyl, $X_1$ represents terminally bonded $C_1$–$C_7$-alkylidene, such as methylene, isobutylidene or isopentylidene, $X_2$ represents oxoethylene bonded via the carbonyl group to the partial structure —N($R_2$)— and $R_2$ represents hydrogen, $C_1$–$C_7$-alkyl or a group of the formula Ia wherein $X_4$ represents $C_1$–$C_7$-alkylidene and $R_3$ represents hydrogen or a phenyl or naphthyl radical that is unsubstituted or mono- or di-substituted by $C_1$–$C_4$-alkyl, $C_1$–$C_4$-alkoxy, halogen having an atomic number of up to and including 35 and/or by trifluoromethyl, and to their salts, especially pharmaceutically acceptable salts.

The invention relates specifically to the compounds of the formula I mentioned in the Examples and to their salts, especially pharmaceutically acceptable salts.

The invention also relates to a process for the manufacture of compounds of the formula I and their salts which is based on methods known per se. This process is characterised in that (a) compounds of the formulae

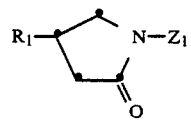

(II)

and

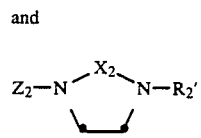

(III)

wherein $Z_1$ represents a group of the formula —$X_1$—C(=O)—$Z_3$ (IIa) and $Z_2$ represents hydrogen, or $Z_1$ represents hydrogen and $Z_2$ represents a group of the formula —C(=O)—$X_1$—$Z_4$ (IIIa), wherein each of $Z_3$ and $Z_4$ represents a removable radical and $R_2'$ represents a radical $R_2$ or an amino-protecting group, or their salts, are condensed with one another, or (b) a compound of the formula

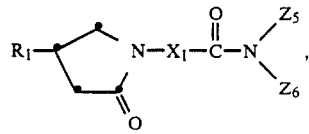

(IV)

wherein $Z_5$ represents a group of the formula

—CH$_2$—CH$_2$—N($R_2'$)—CH$_2$—$Z_4$    (IVa)

—CH$_2$—CH$_2$—N($R_2'$)—CH$_2$CH$_2$—$Z_4$    (IVb)

—CH$_2$—CH$_2$—N($R_2'$)—C(=O)—CH$_2$—$Z_4$    (IVc)

or

—CH$_2$—CH$_2$—N($R_2'$)—CH$_2$—C(=O)—$Z_3$    (IVd)

and $Z_6$ represents hydrogen, or $Z_5$ represents a group of the formula —$X_2$—N($R_2'$)—H (IVe) and $Z_6$ represents a group of the formula —CH$_2$CH$_2$—$Z_4$ (IVg)

or $Z_5$ represents a group of the formula —CH$_2$CH$_2$—N($R_2'$)—H (IVh) and $Z_6$ represents a group of the formula —CH$_2$—$Z_4$ (IVi), —CH$_2$CH$_2$—$Z_4$ (IVg), —C(=O)—CH$_2$—$Z_4$ (IVj) or —CH$_2$—C(=O)—$Z_3$ (IVk), or $Z_5$ represents a group of the formula —CH$_2$—CN (IVl) and $Z_6$ represents a group of the formula —CH$_2$CH$_2$—OH (IVm) or —C(=O)—CH$_2$—OH (IVn), or its salts, or a compound of the formula

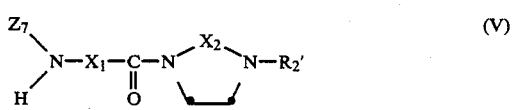

wherein $Z_7$ represents a group of the formula —CH$_2$—CH(R$_1$)—CH$_2$—C(=O)—Z$_3$ (Va) or —C(=O)—CH$_2$—CH(R$_1$)—CH$_2$—Z$_4$ (Vb), or its salts, is cyclised intramolecularly, each of $Z_3$ and $Z_4$ representing a removable radical and $R_2'$ representing a radical $R_2$ or an amino-protecting group, or (c) compounds of the formulae R$_1$—CH(CH$_2$Z$_4$)—CH$_2$—C(=O)—Z$_3$ (VIa), or

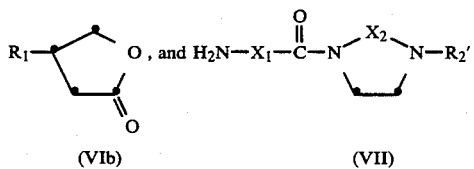

are condensed with one another and an amino-protecting group $R_2'$ which may be present is removed, if necessary an isomeric mixture obtainable in accordance with the process is separated into its components and the isomer of the formula I is isolated and, if desired, a compound obtainable in accordance with the process is converted into a different compound of the formula I, an enantiomeric or diastereoisomeric mixture obtainable in accordance with the process is separated into its components, and/or a free compound obtainable in accordance with the process is converted into a salt, or a salt obtainable in accordance with the process is converted into the free compound or into a different salt.

Removable radicals $Z_3$ and $Z_4$ are, for example, reactive esterified hydroxy groups, and removable radicals $Z_3$ may also be free or etherified hydroxy groups or, in the second place, amino or ammonio groups.

As reactive esterified hydroxy groups there come into consideration, for example, halogen atoms, and in the case of $Z_4$ also sulphonyloxy groups. Halogen $Z_3$ is, for example, chlorine and halogen $Z_4$ is, for example, chlorine, bromine or iodine. Sulphonyloxy $Z_4$ is, for example, sulphonyloxy derived from an organic sulphonic acid or a halosulphonic acid, such as lower alkanesulphonyloxy, for example methane- or ethane-sulphonyloxy, optionally substituted benzene-sulphonyloxy, for example benzene-, p-bromobenzene- or p-toluene-sulphonyloxy, or fluorosulphonyloxy.

Etherified hydroxy $Z_3$ is, for example, hydroxy etherified by N-hydroxysuccinimide or an aliphatic, araliphatic or aromatic alcohol, such as 1-(2,5-dioxo)pyrrolidinoxy, lower alkoxy, for example methoxy, ethoxy, isopropoxy or tertiary butoxy, phenyl-lower alkoxy, for example benzyloxy, or optionally substituted phenoxy, for example phenoxy, pentachlorophenoxy, p-nitrophenoxy or 2,4-dinitrophenoxy.

As amino groups $Z_3$ there come into consideration primary, secondary and tertiary amino groups, such as amino, mono- or di-lower alkylamino, for example methylamino, ethylamino or dimethylamino, lower alkyleneamino or aza-, oxa- or thia-lower alkyleneamino, for example 1-pyrrolidinyl, 1-piperidinyl or 1-morpholinyl, or optionally substituted anilino, for example anilino, p-nitroanilino or 2,4-dinitroanilino, and also 1-imidazolyl groups.

Ammonio groups $Z_3$ are, for example, quaternary ammonio groups, such as tri-lower alkylammonio, for example trimethylammonio, triethylammonio or N-isopropyl-N,N-dimethylammonio, or quaternary ammonio groups derived from aromatic nitrogen bases, such as pyridinio.

Salts of the starting materials and intermediates mentioned are, for example, metal salts, such as alkali metal salts, for example sodium, potassium or lithium salts, of compounds II ($Z_1$=H or $Z_3$=OH), III ($Z_2$=H) or IV ($Z_5$=IVd) or acid addition salts, for example hydrochlorides or hydrobromides, of compounds III ($Z_2$=H) or IV ($Z_5$=IVa, IVb, IVc, IVd; $Z_6$=H, or $Z_5$=IVh; $Z_6$=IVg, IVi, IVj, IVk, or $Z_5$=IVl; $Z_6$=IVm, IVn).

Suitable amino-protecting groups $R_2'$ are, for example, optionally substituted α-aralkyl groups, such as benzyl groups, or benzyloxycarbonyl groups, esterified or etherified hydroxymethyl groups, such as pivaloyloxymethyl, methoxymethyl, 2-chloroethoxymethyl or benzyloxymethyl, tetrahydropyranyl or tri-lower alkylsilyl, such as trimethylsilyl. The protecting group is introduced, for example, by reacting the compound to be protected with a corresponding halogen derivative or with chloroiodomethane (Cl—CH$_2$I), an alkali metal (for example sodium) pivalate, methoxide, 1,2-dichloroethoxide or benzylalcoholate, or with dihydropyrane. Protected amino is accordingly, for example, silylamino, such as tri-lower alkylsilylamino, for example trimethylsilylamino, but may also be phenyl-, diphenyl- or triphenyl-lower alkylamino, such as benzylamino, diphenylmethylamino or tritylamino.

The reactions in accordance with the process and the manufacture of novel starting materials and intermediates are carried out analogously to the manner in which known starting materials and intermediates are reacted and formed. The appropriate customary auxiliaries, such as catalysts, condensation and solvolysis agents and/or solvents or diluents, and reaction conditions, such as temperature and pressure conditions, and also, where appropriate, protective gases, are used, even if this is not expressly mentioned hereinafter.

The condensation of compounds II and III in accordance with process variant (a) and the cyclisation of compounds IV or V in accordance with process variant (b) are effected in customary manner; starting from compounds II and III and from compounds IV wherein $Z_3$ is reactive esterified or etherified hydroxy and/or $Z_4$ is reactive esterified hydroxy, as the case may be, they are effected, for example, in the presence of a basic condensation agent or by using the reactant II or III wherein $Z_1$ or $Z_2$, respectively, is hydrogen, or a compound IV wherein $Z_5$ contains a group of the formula —NH—R$_2$ and $Z_6$ is hydrogen, in the form of a metal salt; starting from compounds IV wherein $Z_5$ represents a group of the formula IVl and $Z_6$ represents a group IVm or IVn, they are effected, especially, in the presence of an acidic agent, and, starting from compounds II or IV wherein $Z_3$ is hydroxy, they are effected, for example, with dehydration of the ammonium salt formed initially, for example by dry heating, for example at from approximately 60° to approximately 180° C., or, especially, by treatment with a water-binding agent.

Basic condensation agents are, for example, alkali metal hydrides, such as sodium hydride, alkali metal amides, such as sodium amide, or alkali metal amides derived from sterically hindered aliphatic secondary amines, for example lithium N,N-diisopropylamide, and also alkali metal lower alkoxides, such as potassium tertiary butoxide, and also sodium methoxide.

Alkali metal or alkaline earth metal hydroxides, such as sodium or potassium hydroxide, and also organic nitrogen bases, such as tri-lower alkylamines, for example triethylamine, or tertiary aromatic nitrogen bases, for example pyridine, are also suitable for the reaction of compounds II and III wherein $Z_1$ is a group $-X_1-C(=O)-Z_3$ (IIa), $Z_2$ is hydrogen, $X_2$ does not have an oxo group in the α-position with respect to the group $Z_2-N<$ and $Z_3$ is reactive esterified hydroxy, and also for the cyclisation of compounds IV wherein $Z_5$ represents a group IVf in which $X_2$ does not have an oxo group in the α-position with respect to the group $-N(R_2)-H$, and $Z_6$ represents a group IVg, or $Z_5$ represents a group IVi in which $X_3$ represents methylene, and $Z_6$ represents a group IVg, and $Z_3$ is reactive esterified hydroxy.

Acidic condensation agents are, for example, strong protonic acids, such as mineral acids, for example sulphuric acid in acetic acid or dibutyl ether, or hydrochloric acid in diethyl or methyl tertiary butyl ether.

Water-binding agents are, for example, carbodiimides, such as N,N'-dicyclohexylcarbodiimide, or halides or esters of carbonic acid or, especially, of oxyacids of sulphur or phosphorus, such as di-lower alkyl carbonates or di-lower alkyl pyrocarbonates, for example diethyl pyrocarbonate, phosgene, di-lower alkyl sulphites, for example dimethyl sulphite, or tri-lower alkyl phosphites, for example trimethyl phosphite, or, especially, optionally substituted triphenyl phosphites, for example triphenyl phosphite.

Starting materials II can be manufactured, for example, by cyclising a corresponding 4-amino-3-$R_1$-butyric acid lower alkyl ester, for example by treatment with sulphuric acid or ethanolic hydrochloric acid, to form the corresponding 4-$R_1$-pyrrolidin-2-one (II; $Z_1$=H) and, to produce compounds II wherein $Z_1$ represents a group IIa, reacting the latter in the presence of a basic condensation agent, for example sodium methoxide, with a compound of the formula $Z_4-X_1-C(=O)-Z_3$ (VIII), wherein $Z_4$ represents iodine, bromine or chlorine and $Z_3$ represents especially lower alkoxy, for example methoxy, if necessary hydrolysing the reaction product (II; $Z_1$=IIa; $Z_3$=etherified hydroxy) to form the corresponding acid (II; $Z_1$=IIa; $Z_3$=hydroxy), for example by treatment with sodium hydroxide solution, if necessary halogenating this acid, for example by means of thionyl chloride, and, if necessary, condensing the reaction product (II; $Z_1$=IIa; $Z_3$=halogen, for example chlorine) with ammonia or an amine of the formula $Z_3-H$ (IX).

Starting materials III wherein $Z_2$ and $R_2$ represent hydrogen are all known. Starting materials III wherein $Z_2$ represents hydrogen and $R_2$ represents lower alkyl or a group of the formula Ia can be obtained, for example, by reacting an imino-di(acetic acid) di-lower alkyl ester or benzylimino-di(acetic acid) di-lower alkyl ester with a lower alkylamine or with a compound of the formula

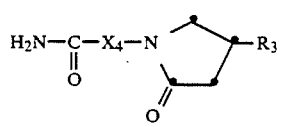

(XXX)

respectively, and optionally removing the 4-protecting group by hydrogenolysis, or by reacting imidazole, piperazine or piperazine-2,5-dione with a reactive ester of a lower alkanol, such as a lower alkyl halide or lower alkyl p-toluenesulphonate, or with a compound of the formula

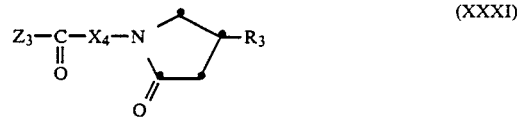

(XXXI)

wherein $Z_3$ has one of the meanings indicated and represents, for example, chlorine, or by condensing a compound of the formula $$H_2N-CH_2CH_2-NH-R_3 \qquad (XXXII)$$

with formaldehyde or with a reactive derivative thereof, for example dimethoxymethane.

Starting materials III wherein $Z_2$ represents a group IIIa can be obtained starting from the corresponding compounds III, for example such as those mentioned above, wherein $Z_2$ is hydrogen, by condensation with compounds of the formula $Z_4-X_1-C(=O)-Z_3$ (VIII; $Z_3$=halogen).

In a preferred embodiment of process variant (a), the starting material used is, for example, a compound of the formula II wherein $Z_1$ represents a group of the formula $-X_1-C(=O)-Z_3$ (IIa; $Z_3$=OH), and this compound is reacted in the presence of a phosphorous acid ester, for example triphenyl phosphite, with a compound of the formula III wherein $Z_2$ represents hydrogen. The reactant II is preferably obtained by reacting the corresponding 4-$R_1$-pyrrolidin-2-one with a corresponding compound of the formula $Z_4-X_1-C(=O)-Z_3$ (VIII; $Z_4$=bromine, $Z_3$=lower alkoxy, for example methoxy) in the presence of an alkali metal lower alkoxide, for example sodium methoxide, and subsequently hydrolysing the resulting ester (II; $Z_1$=IIa, $Z_3$=lower alkoxy, for example methoxy), for example by treatment with sodium hydroxide solution, and then treating it with acid.

In another preferred embodiment of process variant (a), a compound II wherein $Z_1$ is hydrogen is reacted in the presence of an alkali metal hydride, for example sodium hydride, in dioxan with a compound III wherein $Z_2$ represents a group of the formula IIIa ($Z_4$=chlorine or bromine).

Starting materials IV wherein $Z_5$ represents a group IVa, IVb, IVc or IVd and $Z_6$ represents hydrogen, or $Z_5$ represents a group IVe and $Z_6$ represents a group of the formula IVg, are preferably manufactured in situ and cyclised without being isolated, for example by reacting a compound of the formula

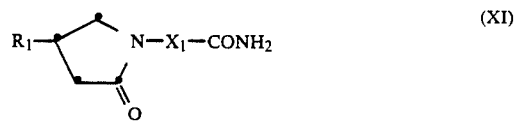

(XI)

with a compound of the formula $$Z_4-CH_2-N(R_2')-CH_2CH_2-Z_4 \qquad (XIIa)$$

$$Z_4-CH_2CH_2-N(R_2')-CH_2CH_2-Z_4 \qquad (XIIb)$$

$Z_4-CH_2-C(=O)-N(R_2')-CH_2CH_2-Z_4$ (XIIc)

or $Z_3-C(=O)-CH_2-N(R_2')-CH_2CH_2-Z_4$ (XIId)

or firstly with a compound of the formula $Z_4-CH_2CH_2-N(R_2')-H$ (XIIIa)

$Z_3-C(=O)-CH_2-N(R_2')-H$ (XIIIb)

$Z_4-CH_2-C(=O)-N(R_2')-H$ (XIIIc)

or $Z_4-CH_2-N(R_2')-H$ (XIIId)

and then with a compound of the formula $Z_4-CH_2CH_2-Z_4$ (XIb)

However, it is also possible to react a compound of the formula

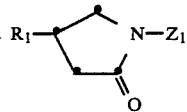 (II)

wherein $Z_1$ represents a group of the formula $-X_1-C(=O)-Z_3$ (IIa)

with a compound of the formula $H_2N-X_2-(R_2')-CH_2CH_2-Z_4$ (XVa), or firstly with a compound of the formula $H_2N-X_2-N(R_2')-H$ (XVIa)

and then with a compound XIVb, or firstly with a compound of the formula $H_2N-CH_2CH_2-N(R_2')-H$ (XVIb)

and then with a compound of the formula $Z_4-CH_2-C(=O)-Z_3$ (XVIIIa) or XIVb.

Starting materials IV wherein $Z_5$ represents a group IVl and $Z_6$ represents a group IVm or IVn are obtained, for example, by reacting aminoacetonitrile with ethylene oxide, if necessary protecting the hydroxy group in the resulting 2-(2-hydroxyethylamino)-acetonitrile, for example by means of acetylation, condensing the reaction product with a compound II wherein $Z_1$ represents a group of the formula $-X_1-C(=O)-Z_3$ (IIa), and, if necessary, removing the protecting group.

The above reactions are preferably carried out in the presence of one of the basic condensation agents mentioned. Each of $Z_3$ and $Z_4$ likewise has the meanings indicated above, $Z_3$ representing especially lower alkoxy or optionally substituted phenoxy and $Z_4$ representing especially chlorine, bromine or iodine or a sulphonyloxy group, for example p-toluenesulphonyloxy.

Intermediates V are also preferably manufactured in situ and cyclised without being isolated, for example by reacting a compound of the formula

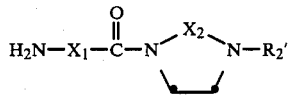 (VII)

under basic conditions with a compound of the formula $Z_4-CH_2-CH(R_1)-CH_2-C(=O)-Z_3$ (VIa)

or with a compound of the formula

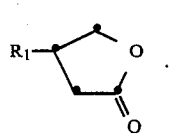 (VIb)

An intermediate V wherein $Z_7$ in the first-mentioned case represents a group Va or Vb and in the second-mentioned case represents a group Vb ($Z_4$=hydroxy) is formed temporarily which reacts further according to the invention.

In a preferred embodiment of process variant (b), a 4-$R_1$-pyrrolidin-2-one (II; $Z_1$=H) is reacted in the presence of an alkali metal alkoxide or an alkali metal hydride, for example in the presence of sodium methoxide or sodium hydride, with a compound of the formula $Z_4-X_1-C(=O)-N(H)-CH_2CH_2-N(R_2')-CH_2CH_2-Z_4$ (XXIVa), $Z_4-X_1-C(=O)-NH-CH_2CH_2-N(R_2')-CH_2-Z_4$ (XXIVb), $Z_4-X_1-C(=O)-NH-CH_2CH_2-N(R_2')-CH_2-C(=O)-Z_3$ (XXIVc)

or $Z_4-X_1-C(=9)-NH-CH_2CH_2-N(R_2')-C(=O)-CH_2-Z_4$ (XXIVd), or firstly with a compound of the formula $Z_4-X_1-C(=O)-Z_3$ (VIII; $Z_4$=chlorine or bromine, $Z_3$=amino) and then with a compound of the formula $Z_4-CH_2-N(R_2')-CH_2CH_2-Z_4$ (XXVa), $Z_4-CH_2-N(R_2')-CH_2CH_2-Z_4$ (XXVb), $Z_4-CH_2-C(=O)-N(R_2')-CH_2-CH_2-Z_4$ (XXVc) or $Z_3-C(=O)-CH_2-N(R_2')-CH_2CH_2-Z_4$ (XXVc). An intermediate IV wherein $Z_5$ represents a group IVa, IVb, IVc or IVd and $Z_6$ represents hydrogen is formed temporarily and can be isolated if the reaction is carried out in the presence of an alkali metal alkoxide, or reacts further according to the invention if the reaction is carried out in the presence of an alkali metal hydride.

In another preferred embodiment of process variant (b), a compound of the formula IV ($Z_5$=IVl, $Z_6$=IVm or IVn), which can be obtained, for example, by reacting a compound II ($Z_1$=IIa, $Z_3$=amino) firstly with 2-iodoethanol or a glycolic acid lower alkyl ester and then with chloroacetonitrile, is treated with an acidic condensation agent, for example with sulphuric acid, analogously to the known Ritter reaction.

In a further preferred embodiment of process variant (b), a compound III ($Z_2$=IIIa; $Z_4$=halogen) is reacted with an acid of the formula $H_2N—CH_2—CH(R_1)—CH_2—C(=O)—Z_3$ (XXVI; $Z_3$=OH) or a reactive carboxy derivative thereof, such as the halide or an ester, for example a lower alkyl ester or an optionally substituted, such as p-nitrated, phenyl ester, thereof An intermediate V ($Z_7$=Va) is formed temporarily which cyclises according to the invention under the basic conditions mentioned.

The reaction of compounds VIa or VIb in accordance with process variant (c) is effected in customary manner; starting from compounds VIa it is effected, for example, under neutral or basic conditions, that is to say in an inert solvent, if necessary while heating, and, starting from compounds VIb, it is effected, for example, in the presence of an acidic condensation agent. Basic condensation agents are, for example, alkali metal hydrides, such as sodium hydride, alkali metal amides, such as sodium amide, or alkali metal amides derived from sterically hindered aliphatic secondary amines, for example lithium N,N-diisopropylamide, alkali metal lower alkoxides, such as potassium tertiary butoxide, and also sodium methoxide, alkali metal or alkaline earth metal hydroxides, such as sodium or potassium hydroxide, and also organic nitrogen bases, such as tri-lower alkylamines, for example triethylamine, or tertiary aromatic nitrogen bases, for example pyridine. Acidic condensation agents are, for example, strong protonic acids, such as mineral acids, for example sulphuric acid or hydrochloric acid.

Starting materials VIa and VIb are manufactured, for example, by reacting a compound of the formula $R_1—CH_2—CH=O$ (XXI), after metallation in the α-position, for example by treatment with an alkali metal hydride or an alkali metal lower alkoxide, with a compound of the formula $Z_4—CH_2—C(=O)—Z_3$ (XXII; $Z_3$=lower alkoxy; $Z_4$=halogen) and treating the reaction product with a reducing agent suitable for the reduction of the formyl group to hydroxymethyl, for example with sodium cyanoborohydride. The resulting hydroxy ester VIa, if necessary after preliminary treatment with a halogenation agent, such as phosphorus tribromide and pyridine, can then be reacted with the reactant under neutral or basic conditions or can be cyclised under acidic conditions to form the corresponding compound VIb.

Starting materials VII are obtained, for example, by condensing with one another compounds of the formulae $H_2N—X_1—C(=O)—Z_3$ (XXIII; $Z_3$=lower alkoxy or optionally substituted phenoxy) and

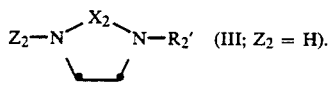

(III; $Z_2$ = H).

The freeing of intermediately protected radicals, for example the removal of an amino-protecting group $R_2'$, is effected in customary manner, for example by hydrogenolysis, for example in the presence of platinum or palladium catalysts, or by solvolysis, such as mild hydrolysis, for example treatment with water under neutral or weakly acidic conditions, for example by the action of dilute-aqueous mineral or carboxylic acids, for example dilute hydrochloric or acetic acid.

Compounds obtainable in accordance with the process can be converted in customary manner into different compounds of the formula I.

For example, substituents can be introduced into the radical $R_1$ of the compounds; lower alkyl can be introduced, for example, by reaction with a lower alkyl halide in the presence of aluminium trichloride, lower alkoxy can be introduced, for example, by nitration, reduction of the nitro group to the amino group, diazotisation of the latter and treatment of the diazonium salt formed with the corresponding lower alkanol while heating, and halogen can be introduced, for example, by treatment with chlorine or bromine, advantageously in the presence of a Lewis acid, for example iron(III) chloride. However, it is also possible to replace halogen by trifluoromethyl, for example by treatment with trifluoroiodomethane in the presence of copper powder or copper(I) iodide.

Furthermore, compounds of the formula I wherein $R_2$ is hydrogen can be substituted by a radical $R_2$ other than hydrogen, for example by reaction with a lower alkyl halide or a compound of the formula

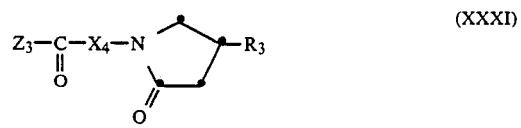

(XXXI)

wherein $Z_3$ has one of the meanings indicated and represents, for example, chlorine, in the presence of a base specified for process variants (a) and (b), such as sodium hydride. Conversely, lower alkyl $R_2$ can be replaced by hydrogen, for example by treatment with a haloformic acid lower alkyl ester and subsequent hydrolysis.

Depending on the starting materials and procedures chosen, the novel compounds may be in the form of one of the possible isomers, for example, depending on the number of asymmetric carbon atoms, they may be in the form of optical isomers, such as in the form of an enantiomer, such as an antipode or diastereoisomer, or in the form of mixtures thereof, such as enantiomeric mixtures, for example racemates, diastereoisomeric mixtures or mixtures of racemates.

Resulting diastereoisomeric mixtures and mixtures of racemates can be separated in known manner into the pure diastereoisomers or racemates on the basis of the physico-chemical differences between the components, for example by chromatography and/or fractional crystallisation. Resulting racemates can also be resolved into the optical antipodes by known methods, for example by recrystallisation from an optically active solvent, with the aid of microorganisms or by reacting a compound of the formula I with an optically active acid or an anhydride thereof, or with a reactive ester of an optically active alcohol, and separating the resulting diastereoisomeric ester, for example on the basis of different solubilities, into the diastereoisomers, from which the enantiomers can be freed by the action of suitable agents. Racemate compounds of the formula I can also be separated into diastereoisomeric mixtures by reaction with an optically active auxiliary compound, for example with an optically active acid to form mixtures of diastereoisomeric salts, and separation of the latter into the diastereoisomers, from which the enantiomers can be freed in the manner customary in each particular case.

Optically active acids customary for this purpose are, for example, optically active carboxylic or sulphonic acids, such as D- or L-tartaric acid, di-o-toluoyltartaric acid, malic acid, mandelic acid, camphorsulphonic acid or quinic acid.

Furthermore, resulting free, salt-forming compounds can be converted into salts in a manner known per se, for example by reacting a solution of the free compound in a suitable solvent or solvent mixture with a corresponding acid or with a suitable ion exchanger.

Resulting salts can be converted into the free compounds in a manner known per se, for example by treatment with a base, such as an alkali metal hydroxide, a metal carbonate or hydrogen carbonate, or ammonia.

Resulting salts can be converted into different salts in a manner known per se, for example by treating a salt of an organic acid with a suitable metal salt, such as a sodium, barium or silver salt, of an acid in a suitable solvent in which an inorganic salt that forms is insoluble and therefore separates out of the reaction mixture.

The compounds, including their salts, can also be obtained in the form of hydrates or include the solvent used for crystallisation.

Owing to the close relationship between the novel compounds in free form and in the form of their salts, hereinbefore and hereinafter there is to be understood by the free compounds or their salts, where appropriate with regard to meaning and purpose, optionally also the corresponding salts or free compounds, respectively.

The invention also relates to those forms of the process according to which compounds obtainable as intermediates at any stage of the process are used as starting materials and the remaining steps are carried out, or a starting material is used in the form of a salt or, especially, is formed under the reaction conditions.

For example, as mentioned, in accordance with process variant (b) intermediates of the formulae IV and V can be formed in situ and reacted further without being isolated.

The invention also relates to novel starting materials developed specifically for the manufacture of the compounds according to the invention, especially the group of starting materials that result in the compounds of the formula I characterised at the beginning as being preferred, to processes for their manufacture, and to their use as intermediates.

The novel compounds of the formula I can be used, for example, in the form of pharmaceutical preparations that contain a therapeutically effective amount of the active ingredient, optionally together with inorganic or organic, solid or liquid pharmaceutically acceptable carriers that are suitable for enteral, for example oral, or parenteral administration. Thus, there are used tablets or gelatine capsules that contain the active ingredient together with diluents, for example lactose, dextrose, sucrose, mannitol, sorbitol or cellulose, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat, rice or arrowroot starch, gelatine, tragacanth, methyl-cellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colourings, flavourings or sweeteners. Furthermore, the novel compound of the formula I can be used in the form of preparations that can be administered parenterally or in the form of infusion solutions. Such solutions are preferably isotonic aqueous solutions or suspensions, it being possible to prepare these before use, for example in the case of lyophilised preparations that contain the active ingredient on its own or together with a carrier, for example mannitol. The pharmaceutical preparations may be sterilised and/or may contain adjuncts, for example preservatives, stabilisers, wetting agents and/or emulsifiers, solubilisers, salts for regulating the osmotic pressure and/or buffers. The present pharmaceutical preparations, which, if desired, may contain further pharmacologically active substances, are manufactured in a manner known per se, for example by means of conventional mixing, granulating, confectioning, dissolving or lyophilising processes, and contain approximately from 0.1% to 100%, especially from approximately 1% to approximately 50% or, in the case of lyophilisates, up to 100%, active ingredient.

The invention also relates to the use of the compounds of the formula I, preferably in the form of pharmaceutical preparations. The dosage can depend on various factors, such as the mode of administration, and the species, age and/or individual condition. The doses to be administered daily are, in the case of oral administration, from approximately 0.25 to approximately 10 mg/kg and, for warm-blooded animals weighing approximately 70 kg, they are preferably from approximately 20 mg to approximately 500 mg.

The following Examples serve to illustrate the invention; temperatures are given in degrees Celsius and pressures in mbar.

EXAMPLE 1

82.5 g (325 mmol) of 2-[4-(p-chlorophenyl)-2-oxopyrrolidin-1-yl]-acetic acid, 32.5 g (325 mmol) of piperazin-2-one (ketopiperazine) and 100.8 g (325 mmol) of freshly distilled triphenyl phosphite are melted at 180°. The whole is allowed to cool to 130° and left to stand for 5 hours. The solidified reaction mass is cooled to room temperature and stirred for 1 hour with 300 ml of dichloromethane. The whole is filtered with suction, washed three times with 150 ml of dichloromethane each time and allowed to dry in the air. 1-[4-(p-chlorophenyl)-2-oxopyrrolidin-1-ylacetyl]-3-oxopiperazine having a melting point of 208°–210° is obtained and can be purified further by dissolving in 200 ml of hot acetic acid, adding 800 ml of water and crystallising in an ice bath.

The starting material can be manufactured, for example, as follows:

13 g (565 mmol) of sodium are added in portions to 410 ml of ethanol. After it has dissolved completely, 107 g (545 mmol) of 4-(p-chlorophenyl)-2-oxopyrrolidine are added, the whole is stirred at room temperature for 2 hours, concentrated to dryness by evaporation under reduced pressure and dried overnight at 100° under reduced pressure. The resulting sodium 4-(p-chlorophenyl)-2-oxopyrrolidine is made into a slurry in 340 ml of toluene, and a solution of 63.7 ml (95.9 g; 574 mmol) of bromoacetic acid ethyl ester is added dropwise, while stirring, at 20° to 25°. The whole is stirred for a further 16 hours, concentrated to dryness by evaporation under reduced pressure at approximately 70° and partitioned between 300 ml of water and 600 ml of ethyl acetate. The organic phase is separated off, washed with saturated sodium chloride solution, dried over sodium sulphate, filtered and concentrated to dryness by evaporation under reduced pressure. 2-[4-(p-chlorophenyl)-2-oxopyrrolidin-1-yl]-acetic acid ethyl ester is obtained which, for purification, is distilled under reduced pressure; b.p.=176°–178° at 0.02 torr (0.027 mbar).

95.6 g (340 mmol) of 2-[4-(p-chlorophenyl)-2-oxopyrrolidin-1-yl]-acetic acid ethyl ester are dissolved in 440 ml of methanol; 22.5 g (40 mmol) of potassium hydroxide (80% strength) are added and the whole is heated under reflux for 16 hours. Concentration by evaporation is carried out under reduced pressure at 70°, 200 ml of hydrochloric acid are added and the whole is extracted by shaking with 800 ml of ethyl acetate. The organic phase is washed with saturated sodium chloride solution, concentrated to 500 ml, and 200 ml of hexane are added. The crystalline precipitate is filtered off with suction and dried. 2-[4-(p-chlorophenyl)-2-oxopyrrolidin-1-yl]-acetic acid having a melting point of 142°-43° is obtained. Additional product can be obtained by concentrating the mother liquor by evaporation, taking up the residue in 200 ml of ethyl acetate and crystallising it by the addition of 100 ml of hexane.

EXAMPLE 2

4.46 g (44.6 mmol) of piperazin-2-one (ketopiperazine) and 300 ml of dimethylformamide are added to 22.4 g (44.6 mmol) of 2-[4-(p-chlorophenyl)-2-oxopyrrolidin-1-yl]-acetic acid pentachlorophenyl ester and the whole is stirred for 5 hours at room temperature. The whole is concentrated to dryness by evaporation under reduced pressure at 70°, stirred with 150 ml of ethyl acetate for 1 hour and then 150 ml of diethyl ether are added; the whole is filtered with suction, washed with 50 ml of diethyl ether and allowed to dry. 1-[4-(p-chlorophenyl)-2-oxopyrrolidin-1-ylacetyl]-3-oxopiperazine having a melting point of 205°-207° is obtained and can be purified further by recrystallisation from 300 ml of butanol, washing with 50 ml of diethyl ether and drying, and then melts at 208°-210°.

The starting material can be manufactured, for example, as follows:

73.5 g (290 mmol) of 2-[4-(p-chlorophenyl)-2-oxopyrrolidin-1-yl]-acetic acid are suspended in 900 ml of tetrahydrofuran; 92.5 g (350 mmol) of pentachlorophenol are added and the whole is stirred at room temperature until a clear solution is obtained. The solution is cooled in an ice bath, 65.8 g (319 mmol) of dicyclohexylcarbodiimide dissolved in 180 ml of tetrahydrofuran are added dropwise thereto within a period of 30 minutes and the whole is stirred for a further 1 hour in the ice bath and for a further 16 hours at room temperature; the resulting dicyclohexylurea is filtered off and the filtrate is concentrated to dryness by evaporation under reduced pressure at 60° and recrystallised from 400 ml of ethyl acetate. 2-[4-(p-chlorophenyl)-2-oxopyrrolidin-1-yl]-acetic acid pentachlorophenyl ester having a melting point of 135°-136° is obtained. Additional product can be obtained by concentrating the mother liquor.

EXAMPLE 3

10 g (30 mmol) of N-[4-(p-fluorophenyl)-2-oxopyrrolidin-1-ylacetoxy]-succinimide and 3.0 g (30 mmol) of piperazin-2-one (ketopiperazine) are stirred at room temperature in 100 ml of dimethylformamide for 16 hours. The whole is concentrated to dryness by evaporation at 70° under reduced pressure, extracted at boiling temperature with trichloromethane, allowed to cool, filtered with suction and allowed to dry in the air. 1-[4-(p-fluorophenyl)-2-oxopyrrolidin-1-ylacetyl]-3-oxopiperazine having a melting point of 200°-203° is obtained.

The starting material can be manufactured, for example, as follows:

A total of 31.5 g (150 mmol) of dicyclohexylcarbodiimide is added in portions to a solution of 35.6 g (150 mmol) of 2-[4-(p-fluorophenyl)-2-oxopyrrolidin-1-yl]-acetic acid and 17.2 g (150 mmol) of N-hydroxysuccinimide in 570 ml of dioxan, during which operation the temperature of the reaction mixture should be maintained below 30° by cooling in an ice bath. When the exothermic reaction has ceased, the reaction mixture is stirred for 16 hours at room temperature, the precipitated dicyclohexylurea is filtered off and the filtrate is concentrated to dryness by evaporation under reduced pressure at 70°. The residue is dissolved in 200 ml of ethyl acetate, and diethyl ether is added until the solution starts to turn cloudy. The crystalline precipitate which forms directly is filtered off with suction, washed with diethyl ether and dried. N-[4-(p-fluorophenyl)-2-oxopyrrolidin-1-ylacetoxy]-succinimide having a melting point of 120°-123° is obtained.

EXAMPLE 4

A mixture of 10 g (3.7 mmol) of 2-[4-(p-chlorophenoyl)-2-oxopyrrolidin-1-yl]-acetic acid methyl ester and 10 g (100 mmol) of N-methylpiperazine is shaken until it turns red. The mixture is concentrated to dryness by evaporation under reduced pressure at 70°. The oily residue (14.3 g) is dissolved in 100 ml of N hydrochloric acid and the solution is extracted with 100 ml of ethyl ether. The aqueous phase is rendered alkaline with concentrated sodium hydroxide solution and the base thus freed is extracted with 500 ml of methylene chloride. After drying over sodium sulphate, filtering and concentrating by evaporation, 1-[4-(p-chlorophenyl)-2-oxopyrrolidin-1-ylacetyl]-4-methylpiperazine is obtained. The mass spectrogram indicates a molecular weight of 336.

9.9 g of the free base are dissolved in 30 ml of ethanol, adjusted to pH 4 with ethanolic hydrochloric acid and the hydrochloride formed is precipitated by the addition of ethyl ether and filtered with suction. 1-[4-(p-chlorophenyl)-2-oxopyrrolidin-1-ylacetyl]-4-methylpiperazine bis-hydrochloride having a melting point of 202°-204° is obtained.

EXAMPLE 5

A solution of 15.8 g (50 mmol) of N-[2-(2-oxo-4-phenylpyrrolidin-1-yl)-acetoxy]-succinimide and 8.8 g (50 mmol) of N-benzylpiperazine in 100 ml of dimethylformamide is stirred at room temperature for 16 hours. The reaction mixture is freed of the solvent under reduced pressure at 70°. The oily residue (28 g) is taken up in 100 ml of ethyl acetate, washed three times with 50 ml of water each time, extracted by shaking with saturated aqueous sodium chloride solution, dried over sodium sulphate, filtered and concentrated to 30 to 40 ml. The aqueous extracts contain N-hydroxysuccinimide and are discarded. A solution of 5.8 g of maleic acid, dissolved in 100 ml of warm ethyl acetate, is added to the concentrated ethyl acetate layer. The resulting salt first precipitates in the form of an oil but crystallises fully when stirred in an ice bath. After recrystallisation from ethanol, crystalline 1-(2-oxo-4-phenylpyrrolidin-1-ylacetyl)-4-benzylpiperazine maleate having a melting point of 170°-173° is obtained.

19 g of the salt described are made into a slurry with 100 ml of water, covered with a layer of 100 ml of ethyl acetate, and adjusted to pH 8 to 9 with saturated aqueous sodium hydrogen carbonate solution. The ethyl acetate layer is washed with saturated sodium chloride solution, dried over sodium sulphate, filtered and concentrated to dryness by evaporation. Oily 1-[2-(2-oxo-4-phenylpyrrolidin-1-yl)-acetyl]-4-benzylpiperazine having an Rf value of 0.60; eluant toluene/ethanol (1:1), is left behind as the residue.

The oily base is taken up in 300 ml of acetic acid and hydrogenated for 16 hours at 22° in the presence of 1.5 g of 5% palladium-on-carbon. After 860 ml of hydrogen have been absorbed the catalyst is filtered off and the clear filtrate is concentrated to dryness by evaporation under reduced pressure at 70°. The oily residue crystallises when digested with ethyl acetate in an ice bath and is recrystallised from 200 ml of ethyl acetate. 1-[2-(2-oxo-4-phenylpyrrolidin-1-yl)-acetyl]-piperazine diacetate having a melting point of 121°–124° is obtained.

EXAMPLE 6

To a suspension of 6.0 g (23.3 mmol) of 1-[2-(2-oxopyrrolidin-1-yl)-acetyl]-piperazine hydrochloride in 80 ml of methylene chloride there are added firstly 2.6 g (3.6 ml; 25.5 mmol) of triethylamine and then, dropwise, a solution of 13.7 g (23.3 mmol) of 2-[4-(p-chlorophenyl)-2-oxopyrrolidin-1-yl]-acetic acid pentachlorophenyl ester in 30 ml of methylene chloride. After being stirred at 20° for 16 hours, the suspension is filtered with suction. 6.16 g of a white crystalline mass are obtained. 110 ml of ethyl ether are stirred into the filtrate, whereby a further 6.51 g of precipitate can be formed and collected. The two portions are combined, triturated under 200 ml of ethyl ether and filtered with suction, and the resulting product is dissolved in 150 ml of hot glacial acetic acid, and warm water (50°) is added until the solution becomes cloudy. The whole is cooled to 20°; after 3 hours, the resulting crystalline product is filtered off with suction and dried on a water bath. 1-[4-(p-chlorophenyl)-2-oxopyrrolidin-1-ylacetyl]-4-(2-oxopyrrolidin1-ylacetyl)-piperazine having a melting point of 224°–226° is obtained.

The starting material can be manufactured, for example, as follows:

A solution of 14.4 g (60 mmol) of N-[2-(2-oxopyrrolidin-1-yl)-acetoxy]-succinimide and 10.6 g (60 mmol) of 1-benzylpiperazine in 125 ml of dimethylformamide is stirred for 16 hours at 20°. The reaction mixture is concentrated to dryness by evaporation under reduced pressure at 90°. The oily residue is taken up in 250 ml of water, and a solution of 5.4 g of oxalic acid in 5 ml of water is added, and then the whole is stirred in an ice bath. The resulting crystalline oxalate is filtered off with suction, dissolved in 400 ml of water and the pH is adjusted to 9 with concentrated ammonia solution The clear aqueous solution is washed twice with 30 ml of ether each time, the ethereal extracts are discarded and the aqueous layer is concentrated by evaporation under reduced pressure at 70°. The residue is composed of a sticky mass which is stirred into 400 ml of ethanol at 30° and the insoluble matter is filtered off with suction. After concentrating the clear ethanolic filtrate by evaporation, a slightly yellowish oil is obtained. This is boiled in 130 ml of ethyl acetate and filtered while hot, and the filtrate is stirred in an ice bath to complete the reaction. The precipitated crystals are filtered off with suction and dried on a water bath. 1-[2-(2-oxopyrrolidin-1-yl)-acetyl]-4-benzylpiperazine is obtained.

A solution of 13.2 g of this product in 300 ml of glacial acetic acid is hydrogenated for 4 hours at 20° in the presence of 1.5 g of 5% palladium-on-carbon. After 986 ml of hydrogen have been absorbed, the hydrogenation is discontinued, the catalyst is filtered off with suction and the filtrate is concentrated to dryness by evaporation under reduced pressure at 70° The oily residue is dissolved in 200 ml of ethyl acetate and the pH is adjusted to 2 with alcoholic hydrochloric acid. The resulting hydrochloride is filtered off with suction and recrystallised from ethanol. 1-[2-(2-oxopyrrolidin-1-yl)-acetyl]piperazine hydrochloride having a melting point of 232°–234° is obtained. The maleate which can be prepared analogously melts at 163°–165°.

EXAMPLE 7

A mixture of 5.1 g (20.1 mmol) of 2-[4-(p-chlorophenyl)-2-oxopyrrolidin-1-yl]-acetic acid, 3.5 g (20.1 mmol) of 1-benzylpiperazine, 6.57 g (21.1 mmol) of triphenyl phosphite and 15 ml of dimethylformamide is stirred for 3 hours at 95°–100°. The mixture is the concentrated under reduced pressure at 90° until a constant weight is reached. The oily residue is diluted with 40 ml of acetone, and a solution of 2.3 g of maleic acid in 20 ml of acetone is added thereto. The precipitated maleate is filtered off with suction and washed with a little acetone and ethyl ether. The resulting 1-[4-(p-chlorophenyl)-2-oxopyrrolidin-1-ylacetyl]-4-benzylpiperazine maleate having a melting point of 161°–164° is recrystallised from methanol and ether.

14.3 g of the base freed from the maleate are catalytically debenzylated in 150 ml of glacial acetic acid with hydrogen in the presence of 1.5 g of 5% palladium-on-carbon. After 777 ml of hydrogen have been absorbed, the catalyst is filtered off with suction and the filtrate is concentrated by evaporation under reduced pressure at 80°. 60 ml of water and 40 ml of N sodium hydroxide solution are added to the oily residue and the whole is extracted twice with 50 ml of chloroform each time. After drying over sodium sulphate, filtering and concentrating by evaporation, 1-[4-(p-chlorophenyl)-2-oxopyrrolidin-1-ylacetyl]-piperazine is obtained in the form of a yellowish oil which is dissolved in 100 ml of acetone and is converted into the maleate having a melting point of 148°–150° by the addition of 3.4 g of maleic acid.

EXAMPLE 8

7.74 g (25 mmol) of 2-[4-(p-chlorophenyl)-2-oxopyrrolidin-1-yl]-4-methylvaleric acid, 2.75 g (27.5 mmol) of piperazin-2-one and 0.3 g (2.5 mmol) of 4-methylaminopyridine are dissolved in 100 ml of tetrahydrofuran, and a solution of 5.67 g (27.5 mmol) of N,N'-dicyclohexylcarbodiimide in 20 ml of tetrahydrofuran is added dropwise, while stirring, at a temperature of from 10° to 15°. The suspension is stirred for 16 hours at room temperature.

The crystals are filtered off with suction, the filtrate is concentrated by evaporation under reduced pressure, and the oily residue is dissolved in 100 ml of methylene chloride and washed twice with 50 ml of hydrochloric acid each time, twice with sodium hydrogen carbonate solution and twice with 50 ml of water each time. The organic phase is separated off, dried over sodium sulphate, filtered and concentrated to dryness by evaporation under reduced pressure. The product is purified by flash column chromatography. 1-{2-[4-(p-chlorophenyl)-2-oxopyrrolidin-1-yl]-4-methylpentanoyl}-3-oxopiperazine is obtained in the form of a foam.

The starting material can be manufactured, for example, as follows:

4.8 g (208 mmol) of sodium are added in portions to 150 ml of ethanol. After it has dissolved completely, 39.15 g (200 mmol) of 4-(p-chlorophenyl)-2-oxopyrrolidine are added and the whole is stirred for 2 hours at room temperature, concentrated to dryness by evaporation under reduced pressure, made into a slurry 3 times with toluene and concentrated to dryness by evaporation under reduced pressure.

The resulting sodium salt of 4-(p-chlorophenyl)-2-oxopyrrolidone is made into a slurry in 200 ml of toluene, and a solution of 40.2 g (191.3 mmol) of 2-bromo-4-methylvaleric acid methyl ester in 50 ml of toluene is added dropwise, while stirring, at from 20 to 25°. The whole is stirred for a further 16 hours, concentrated to dryness by evaporation under reduced pressure at approximately 50° and partitioned between 200 ml of water and 300 ml of ethyl acetate. The organic phase is separated off, washed with saturated sodium chloride solution, dried over sodium sulphate, filtered and concentrated to dryness by evaporation under reduced pressure 2-[4-(p-chlorophenyl)-2-oxopyrrolidin-1-yl]-4-methylvaleric acid methyl ester is obtained which, for purification, is distilled under reduced pressure in a bulb tube. B.p.=200° at 0.1 torr.

53.3 g (164.6 mmol) of 2-[4-(p-chlorophenyl)-2-oxopyrrolidin-1-yl]-4-methylvaleric acid methyl ester are dissolved in 230 ml of methanol; 10.9 g (164.4 mmol) of potassium hydroxide (85% strength) are added and the whole is heated under reflux for 16 hours. The whole is concentrated by evaporation under reduced pressure at 50°, 230 ml of 2N hydrochloric acid are added, and the resulting suspension is stirred for 1 hour at 5°. The crystals are filtered off with suction, washed with water and dried under reduced pressure at 80°. Recrystallisation from ethyl acetate/hexane yields 46.1 g of 2-[4-p-chlorophenyl)-2-oxopyrrolidin-1-yl]- 4-methylvaleric acid; m.p. 176°–177°.

EXAMPLE 9

It is also possible to manufacture 1-[4-(p-chlorophenyl)-2-oxopyrrolidin-1-ylacetyl]-4-methyl-3-oxopiperazine in a manner analogous to that described in Examples 1 to 7.

EXAMPLE 10

1.77 g of 1-chloroacetyl-3-oxopiperazine are suspended in 500 ml of toluene at 80°. A total of 2.18 g of sodium-4-(p-chlorophenyl)-2-oxopyrrolidin-2-one is then added in three portions. The whole is stirred for 8 hours at 80° and concentrated to dryness by evaporation under reduced pressure at 70°, and a secondary product is distilled off at 150-°155°/0.05 torr; the residue is extracted by boiling with butanol, filtered and concentrated to dryness by evaporation 1.5 g of 1-[4-(p-chlorophenyl)-2-oxopyrrolidin-1-ylacetyl]-3-oxopiperazine having a melting point of 208°–210° are obtained.

EXAMPLE 11

Tablets each containing 50 mg of 1-[4-(p-chlorophenyl)-2-oxopyrrolidin-1-ylacetyl]-3-oxopiperazine can be manufactured as follows:

| Composition (1000 tablets) | |
|---|---|
| Active ingredient | 500.0 g |
| Lactose | 500.0 g |
| Potato starch | 352.0 g |
| Gelatine | 8.0 g |
| Talc | 60.0 g |
| Magnesium stearate | 10.0 g |
| Silica (highly disperse) | 20.0 g |
| Ethanol | q.s. |

The active ingredient is mixed with the lactose and 292 g of potato starch and the mixture is moistened with an alcoholic solution of the gelatine and granulated through a sieve. After drying, the remainder of the potato starch, the talc, the magnesium stearate and the highly disperse silica are mixed in and the mixture is compressed to form tablets each weighing 145.0 mg and containing 50.0 mg of active ingredient, which, if desired, can be provided with dividing notches for finer adjustment of the dosage.

EXAMPLE 12

Lacquer-coated tablets each containing 100 mg of 1-[4-(p-chlorophenyl)-2-oxopyrrolidin-1-yl-acetyl]-3-oxopiperazine can be manufactured as follows:

| Composition (for 1000 tablets) | |
|---|---|
| Active ingredient | 100.00 g |
| Lactose | 100.00 g |
| Corn starch | 70.00 g |
| Talc | 8.50 g |
| Calcium stearate | 1.50 g |
| Hydroxypropylmethylcellulose | 2.36 g |
| Shellac | 0.64 g |
| Water | q.s. |
| Methylene chloride | q.s. |

The active ingredient, the lactose and 40 g of the corn starch are mixed and moistened with a paste prepared from 15 g of corn starch and water (while heating), and granulated. The granulate is dried and the remaining corn starch, the talc and the calcium stearate are added and mixed with the granulate. The mixture is compressed to form tablets (weight: 280 mg) and these are coated with a solution of the hydroxypropylmethylcellulose and the shellac in methylene chloride; final weight of the lacquer-coated tablets: 283 mg.

EXAMPLE 13

In a manner analogous to that described in Examples 11 and 12 it is also possible to manufacture pharmaceutical preparations containing a different compound of the formula I according to Examples 1 to 9.

We claim:

1. A compound of the formula

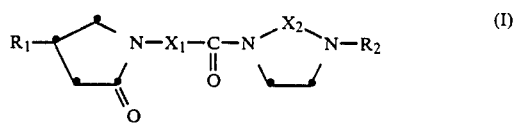

wherein $R_1$ represents a phenyl or naphthyl that is unsubstituted or mono- or di-substituted by at least one of lower alkyl, lower alkoxy, halogen and trifluoromethyl, $X_1$ represents lower alkylidene, $X_2$ represents ethylene or oxoethylene and $R_2$ represents hydrogen, lower alkyl or a radical of the formula

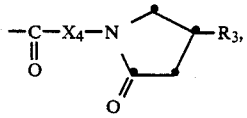

wherein $X_4$ represents lower alkylidene and $R_3$ represents hydrogen or phenyl or naphthyl that is unsubstituted or mono- or di-substituted by at least one of lower alkyl, lower alkoxy, halogen and trifluoromethyl, in free form or in the form of pharmaceutically acceptable salt.

2. A compound according to claim 1 of the formula I, wherein $R_1$ represents phenyl or naphthyl that is unsubstituted or mono- or di-substituted by at least one of $C_1$–$C_4$-alkyl, $C_1$–$C_4$-alkoxy, halogen having an atomic number of up to and including 35 and by trifluoromethyl, $X_1$ represents $C_1$–$C_7$-alkylidene, $X_2$ represents ethylene or oxoethylene and $R_2$ represents hydrogen, $C_1$–$C_7$-alkyl or a group of the formula Ia wherein $X_4$ represents $C_1$–$C_7$-alkylidene and $R_3$ represents hydrogen or phenyl or naphthyl that is unsubstituted or mono- or di-substituted by at least one of $C_1$–$C_4$-alkyl, $C_1$–$C_4$-alkoxy, halogen having an atomic number of up to and including 35 and by trifluoromethyl, or a pharmaceutically acceptable salt thereof.

3. A compound according to claim 1 of the formula I, wherein $R_1$ represents phenyl that is unsubstituted or mono substituted by halogen having an atomic number of up to and including 35, $C_1$–$C_4$-alkoxy, $C_1$–$C_4$-alkyl or by trifluoromethyl, or represents unsubstituted naphthyl, $X_1$ represents terminally bonded $C_1$–$C_7$-alkylidene, $X_2$ represents oxoethylene and $R_2$ represents hydrogen, or a pharmaceutically acceptable salt thereof.

4. A compound according to claim 1 of the formula I, wherein $R_1$ represents phenyl that is unsubstituted or monosubstituted by halogen having an atomic number of up to and including 35, $C_1$–$C_4$-alkoxy, $C_1$–$C_4$-alkyl or by trifluoromethyl, or represents unsubstituted naphthyl, $X_1$ represents terminally bonded $C_1$–$C_4$-alkylidene, $X_2$ represents oxoethylene bonded via the carbonyl group to the partial structure —$N(R_2)$— and $R_2$ represents hydrogen, or a pharmaceutically acceptable salt thereof.

5. A compound according to claim 1 of the formula I, wherein $R_1$ represents phenyl that is unsubstituted or substituted by halogen having an atomic number of up to and including 35, $C_1$–$C_4$-alkoxy, $C_1$–$C_4$-alkyl or by trifluoromethyl, or represents unsubstituted naphthyl, $X_1$ represents terminally bonded $C_1$–$C_4$-alkylidene, $X_2$ represents ethylene and $R_2$ represents $C_1$–$C_4$-alkyl or a group of the formula Ia wherein $X_4$ is terminally bonded $C_1$–$C_4$-alkylidene, and $R_3$ represents hydrogen, or a pharmaceutically acceptable salt thereof.

6. A compound according to claim 1 of the formula I, wherein $R_1$ represents phenyl that is unsubstituted or monosubstituted by halogen having an atomic number of up to and including 35 or represents unsubstituted naphthyl, $X_1$ represents terminally bonded $C_1$–$C_4$-alkylidene, $X_2$ represents oxoethylene bonded via the carbonyl group to the partial structure —$N(R_2)$— and $R_2$ represents hydrogen, or a pharmaceutically acceptable salt thereof.

7. A compound according to claim 1 of the formula I, wherein $R_1$ represents phenyl that is unsubstituted or monosubstituted by halogen having an atomic number of up to and including 35 or represents unsubstituted naphthyl, $X_1$ represents terminally bonded $C_1$–$C_7$-alkylidene, $X_2$ represents oxoethylene bonded via the carbonyl group to the partial structure —$N(R_2)$— and $R_2$ represents hydrogen, or a pharmaceutically acceptable salt thereof.

8. A compound according to claim 1 being 1-[4-(p-chlorophenyl)-2-oxopyrrolidin-1-ylacetyl]-3-oxopiperazine or a salt thereof.

9. A compound according to claim 1 being 1-[4-(p-fluorophenyl)-2-oxopyrrolidin-1-ylacetyl]-3-oxopiperazine or a pharmaceutically acceptable salt thereof.

10. A compound according to claim 1 being 1-[4-(p-chlorophenyl)-2-oxopyrrolidin-1-ylacetyl]-4-methylpiperazine or a pharmaceutically acceptable salt thereof.

11. A compound according to claim 1 being 1-[2-oxo-4-phenylpyrrolidin-1-ylacetyl)-4-benzylpiperazine or a pharmaceutically acceptable salt thereof.

12. A compound according to claim 1 being 1-[4-(p-chlorophenyl)-2-oxopyrrolidin-1-ylacetyl]-4-(2-oxopyrrolidin-1-ylacetyl)-piperazine or a pharmaceutically acceptable salt thereof.

13. A compound according to claim 1 being 1-[4-(p-chlorophenyl)-2-oxopyrrolidin-1-ylacetyl]-4-benzylpiperazine or a pharmaceutically acceptable salt thereof.

14. A compound according to claim 1 being 1-{2-[4-(p-chlorophenyl)-2-oxopyrrolidin-1-yl]-4-methylpentanoyl}-3-oxopiperazine or a pharmaceutically acceptable salt thereof.

15. A compound according to claim 1 being 1-[4-(p-chlorophenyl)-2-oxopyrrolidin-1-ylacetyl]-4-methyl-3-oxopiperazine or a pharmaceutically acceptable salt thereof.

16. A pharmaceutical composition comprising a nootropically effective amount of a compound according to claim 1 or a pharmaceutically acceptable salt thereof in addition to customary pharmaceutical adjuncts.

17. Method for the treatment of cerebral insufficiency in human or animal body comprising administering a nootropically effective amount of a compound according to claim 1 or a pharmaceutically acceptable salt thereof.

* * * * *